United States Patent
Chodorowski-Kimmes et al.

(10) Patent No.: US 7,153,494 B2
(45) Date of Patent: Dec. 26, 2006

(54) DIBENZOYLMETHANE SUNSCREEN COMPOSITIONS PHOTOSTABILIZED WITH AMPHIPHILIC BLOCK COPOLYMERS

(75) Inventors: Sandrine Chodorowski-Kimmes, Senlis (FR); Francis Xavier Quinn, Paris (FR); Jean-Thierry Simonnet, Cachan (FR)

(73) Assignee: L'Oreal, Paris (FR)

( * ) Notice: Subject to any disclaimer, the term of this patent is extended or adjusted under 35 U.S.C. 154(b) by 423 days.

(21) Appl. No.: 10/688,937

(22) Filed: Oct. 21, 2003

(65) Prior Publication Data

US 2004/0091434 A1 May 13, 2004

Related U.S. Application Data

(60) Provisional application No. 60/452,541, filed on Mar. 7, 2003.

(30) Foreign Application Priority Data

Oct. 21, 2002 (FR) .................................. 02 13103

(51) Int. Cl.
- A61Q 19/04 (2006.01)
- A61Q 19/00 (2006.01)
- A61K 31/74 (2006.01)
- A61K 8/02 (2006.01)
- A61K 8/00 (2006.01)

(52) U.S. Cl. ........................ 424/59; 424/60; 424/78.02; 424/78.08; 424/400; 424/401

(58) Field of Classification Search .................. 424/59, 424/60, 78.02, 78.08, 70.1, 400, 401
See application file for complete search history.

(56) References Cited

U.S. PATENT DOCUMENTS

| 5,607,664 A | | 3/1997 | Ascione et al. |
| 5,849,272 A | * | 12/1998 | Baba et al. .................... 424/59 |
| 5,879,688 A | | 3/1999 | Coury et al. |
| 5,989,529 A | | 11/1999 | Kaplan |
| 6,024,944 A | | 2/2000 | Hansenne |
| 6,106,847 A | | 8/2000 | Ferrero et al. |
| 6,569,409 B1 | | 5/2003 | Hansenne et al. |
| 6,616,946 B1 | * | 9/2003 | Meier et al. ................. 424/489 |
| 6,994,846 B1 | * | 2/2006 | L'Alloret .................. 424/78.18 |
| 2001/0034428 A1 | | 10/2001 | Destarac et al. |
| 2002/0061284 A1 | | 5/2002 | Dupuis |
| 2004/0258721 A1 | | 12/2004 | Bauer et al. |

FOREIGN PATENT DOCUMENTS

| EP | 1 213 006 A1 | 6/2002 |
| EP | 1 291 376 A1 | 3/2003 |
| WO | WO 02/28357 A1 | 4/2002 |
| WO | WO 02/28358 A1 | 4/2002 |

OTHER PUBLICATIONS

French Search Report Corresponding to French Priority Counterpart FR/02/13103, issued Jul. 18, 2003, 2 pages.
Abstract—Kazuyuki et al., "Novel Polymer and Cosmetic Using the Same", Pub. No. 2001288233 A, Oct. 16, 2001.
Tamura, "Functions and applications of O/W type polymeric emulsifier", Fragrance Journal, 1998, pp. 78-83.
Meszaros et al., "Block Copolymer Self-assembly in Two Dimensions: Nanoscale Emulsions and Foams", Faraday Discuss, No. 98, 1994, pp. 283-294.
Tsitsilianis et al., "An Associative Polyelectrolyte End-Capped with Short Polystyrene Chains, Synthesis and Rheological Behavior", Macromolecules, vol. 33, No. 8, 2000, pp. 2936-2943, American Chemical Society.
Khougaz et al., "Micellization in Block Polyelectrolyte Solutions. 3. Statis Light Scattering Characterization", vol. 28, No. 21, Oct. 9, 1995, pp. 7135-7147, American Chemical Society.

* cited by examiner

*Primary Examiner*—Shelley A. Dodson
(74) *Attorney, Agent, or Firm*—Buchanan, Ingersoll & Rooney PC

(57) ABSTRACT

Topically applicable photostable sunscreen/photoprotective compositions contain at least one dibenzoylmethane UV-sunscreen and an effective photostabilizing amount therefor of at least one amphiphilic block copolymer which comprises at least one nonionic hydrophilic polymer block and at least one hydrophobic polymer block, formulated into a topically applicable, cosmetically acceptable medium therefor.

34 Claims, No Drawings

DIBENZOYLMETHANE SUNSCREEN COMPOSITIONS PHOTOSTABILIZED WITH AMPHIPHILIC BLOCK COPOLYMERS

CROSS-REFERENCE TO PRIORITY/PROVISIONAL APPLICATIONS

This application claims priority under 35 U.S.C. § 119 of FR-02/13103, filed Oct. 21, 2002, and of provisional application Ser. No. 60/452,541, filed Mar. 7, 2003, both hereby expressly incorporated by reference. This application is also a continuation of said '541 provisional.

BACKGROUND OF THE INVENTION

1. Technical Field of the Invention

The present invention relates to the photostabilization towards UV radiation of screening systems comprising at least one dibenzoylmethane derivative. The invention also relates to novel compositions, in particular cosmetic compositions for topical application.

2. Description of Background/Related/Prior Art

With the aim of ensuring protection of the skin and keratin materials against UV radiation, antisun compositions comprising UV-A-active and UV-B-active organic screening agents are generally used. The majority of these screening agents are liposoluble.

In this regard, one family of screening agents that is particularly advantageous currently consists of dibenzoylmethane derivatives, and especially 4-(tert-butyl)-4'-methoxydibenzoylmethane, which show high intrinsic absorbing power. These dibenzoylmethane derivatives are products that are already known as UV-A-active screening agents and are described especially in FR-A-2,326,405 and FR-A-2,440,933, and also in EP-A-0,114,607. 4-(tert-Butyl)-4'-methoxydibenzoyl-methane is moreover currently sold under the trademark "PARSOL 1789" by Hoffmann LaRoche.

However, these screening agents, and especially Parsol® 1789, or butylmethoxydibenzoylmethane (INCI name) are products that are relatively sensitive to ultraviolet radiation, i.e., they show a tendency to degrade under the action of this radiation. Thus, this lack of photochemical stability of sunscreens in the face of ultraviolet radiation, to which they are by nature intended to be subjected, does not make it possible to ensure constant protection over prolonged exposure to the sun, such that, in a restricting manner, repeated applications at regular and close intervals must be performed by the user in order to obtain effective protection of the skin against UV rays.

It is known practice to combine sunscreens with certain compounds in order to improve their photostability. Thus, EP-1,093,797 describes a process for improving the stability of at least one dibenzoylmethane derivative towards UV radiation, which entails combining the dibenzoylmethane derivative with an insoluble organic screening agent in micronized form, the mean particle size of which ranges from 0.01 to 2 μm.

EP-0,982,310 describes a process for photostabilizing a dibenzoylmethane derivative with a silane or organosilane compound containing a 2-hydroxy-benzophenone function.

EP-1,043,966 describes a process for photostabilizing a 1,3,5-triazine-based sunscreen with an ethylenically unsaturated compound.

EP-1,096,916 describes a process for photostabilizing a dibenzoylmethane derivative with an amphiphilic thickening copolymer which is not of block type.

However, the sunscreens thus stabilized show insufficient resistance to degradation by UV radiation, and the photostabilization of photosensitive sunscreens towards UV radiation is, at the present time, still a problem that has not yet been solved entirely satisfactorily.

SUMMARY OF THE INVENTION

It has now surprisingly and unexpectedly been determined that by combining a screening system comprising at least one dibenzoylmethane derivative with an effective amount of at least one diblock or triblock amphiphilic copolymer comprising at least one nonionic hydrophilic polymer block and at least one hydrophobic polymer block, it is possible to photostabilize the screening system.

The present invention thus features a process for photostabilizing towards ultraviolet radiation, in particular towards solar radiation, a screening system comprising at least one dibenzoylmethane derivative, the said process being essentially characterized in that it comprises combining the screening system comprising at least one dibenzoylmethane derivative with an effective amount of at least one block amphiphilic (and especially diblock or triblock) copolymer comprising at least one nonionic hydrophilic polymer block and at least one hydrophobic polymer block.

By the term "effective amount" is intended the amount of block copolymer required to improve the photostability of the screening system comprising at least one dibenzoylmethane derivative after a controlled UV exposure of 1 hour of UV-A at 3.2 mW/cm$^2$ (i.e., 11.5 J/cm$^2$) and 1 hour of UV-B of 0.22 mW/cm$^2$ (i.e., 0.79 J/cm$^2$).

This invention also features cosmetic compositions for topical application comprising, in a cosmetically acceptable medium, a screening system comprising at least one dibenzoylmethane derivative combined with an effective photostabilizing amount of certain block copolymers.

Other characteristics, aspects and advantages of the invention will emerge on reading the detailed description that follows.

DETAILED DESCRIPTION OF BEST MODE AND SPECIFIC/PREFERRED EMBODIMENTS OF THE INVENTION

The block copolymers used in the process according to the invention are especially diblock or triblock, preferentially nonionic, amphiphilic block polymers, which can form on contact with water micelles, particles of vesicular type (for example liposomes) or of nanosphere type, or lyotropic liquid-crystal phases of lamellar, cubic (direct or inverse) or hexagonal (direct or inverse) type on contact with water. They are especially of diblock (A-B) or triblock (A-B-A) type, A corresponding to a nonionic hydrophilic polymer block and B to a hydrophobic polymer block. The ratio A/B may be between 1/100 and 50/1.

The nonionic hydrophilic polymer block may be chosen from polyethylene oxide (PEO) and polyvinylpyrrolidone (PVP).

The hydrophobic polymer block may be chosen from polystyrene, poly(tert-butylstyrene), poly(methyl methacrylate), poly(ethyl acrylate), poly(butyl acrylate), poly(butyl methacrylate), poly(vinyl acetate), polycaprolactones, polycaprolactams, polydimethyl-siloxanes, poly($C_3$–$C_6$ alkylene oxides), poly(aspartic acid), poly(lactic acid), poly(glycolic acid), poly-leucine, polybutadiene, polyethylenes, polypropylenes and polybutylenes.

The block copolymer is preferably chosen from the following block copolymers:
polystyrene/polyoxyethylene
polymethyl methacrylate/polyoxyethylene
polybutyl methacrylate/polyoxyethylene
polyoxybutylene/polyoxyethylene
polycaprolactone/polyoxyethylene
polyethylene/polyoxyethylene
polyoxyethylene/polyoxybutylene/polyoxyethylene.

Among the dibenzoylmethane derivatives that may especially be mentioned, in a non-limiting manner, are:
2-methyldibenzoylmethane,
4-methyldibenzoylmethane,
4-isopropyldibenzoylmethane,
4-tertbutyldibenzoylmethane,
2,4-dimethyldibenzoylmethane,
2,5-dimethyldibenzoylmethane,
4,4-diisopropyldibenzoylmethane,
4,4-dimethoxydibenzoylmethane,
4-tert-butyl-4'-methoxydibenzoylmethane,
2-methyl-5-isopropyl-4'-methoxydibenzoylmethane,
2-methyl-5-tert-butyl-4'-methoxydibenzoylmethane,
2,4-dimethyl-4'-methoxydibenzoylmethane,
2,6-dimethyl-4-tert-butyl-4'-methoxydibenzoylmethane.

Among the dibenzoylmethane derivatives mentioned above, the one that is particularly preferred is 4-tert-butyl-4'-methoxydibenzoylmethane (Butyl methoxydibenzoylmethane), sold especially under the trademark "Parsol® 1789" by Hoffmann LaRoche.

The screening system may also contain one or more compounds chosen from 1,3,5-triazine derivatives, cinnamic acid derivatives and amino-substituted hydroxybenzophenones.

The 1,3,5-triazine derivatives in accordance with the invention correspond to the following general formula:

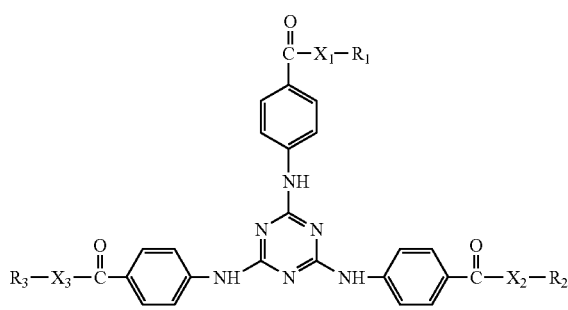

(1)

in which:
$X_1$, $X_2$ and $X_3$, which may be identical or different, represent oxygen or a radical —NR—;
the radicals R, which may be identical or different, denote hydrogen or a linear or branched $C_1$–$C_{18}$ alkyl radical or a $C_5$–$C_{12}$ cycloalkyl radical which may be substituted with one or more $C_1$–$C_4$ alkyl radicals;
$R_1$, $R_2$ and $R_3$, which may be identical or different, are chosen from: hydrogen; a linear or branched $C_1$–$C_{18}$ alkyl radical; a $C_5$–$C_{12}$ cycloalkyl radical optionally substituted with one or more $C_1$–$C_4$ alkyl radicals; a polyoxyethylenated radical comprising from 1 to 6 ethylene oxide units and in which the end OH group is methylated; a radical of formula (2), (3) or (4) below:

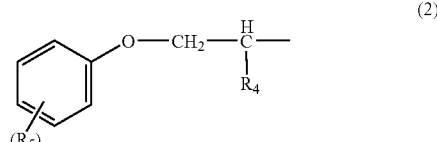

(2)

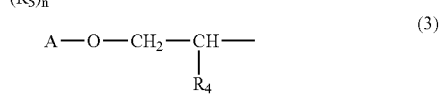

(3)

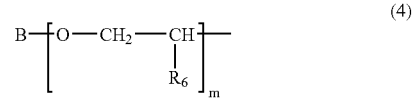

(4)

in which:
$R_4$ is hydrogen or a methyl radical;
$R_5$ is a $C_1$–$C_9$ alkyl radical;
n is an integer ranging from 0 to 3;
m is an integer ranging from 1 to 10;
A is a $C_4$–$C_8$ alkyl radical or a $C_5$–$C_8$ cycloalkyl radical;
B is chosen from: a linear or branched $C_1$–$C_8$ alkyl radical; a $C_5$–$C_8$ cycloalkyl radical; an aryl radical optionally substituted with one or more $C_1$–$C_4$ alkyl radicals;
$R_6$ is hydrogen or a methyl radical.

A first preferred family of 1,3,5-triazine derivatives is the one described in particular in EP-A-0,517,104 (the teachings of which are, as regards the actual definition of these products, entirely included in the present description by way of reference) for the 1,3,5-triazines corresponding to formula (1) above and having all of the following characteristics:
$X_1$, $X_2$ and $X_3$ are identical and represent oxygen;
$R_1$ is chosen from: a $C_5$–$C_{12}$ cycloalkyl radical optionally substituted with one or more $C_1$–$C_4$ alkyl radicals; a radical of formula (2), (3) or (4) above in which:
B is a $C_1$–$C_4$ alkyl radical;
$R_6$ is a methyl radical;
$R_2$ and $R_3$, which may be identical or different, are chosen from: hydrogen; a linear or branched $C_1$–$C_{18}$ alkyl radical; a $C_5$–$C_{12}$ cycloalkyl radical optionally substituted with one or more $C_1$–$C_4$ alkyl radicals; a radical of formula (2), (3) or (4) above in which:
B is a $C_1$–$C_4$ alkyl radical;
$R_6$ is a methyl radical.

A second preferred family of 1,3,5-triazine derivatives according to the invention is the one described in particular in EP-A-0,570,838 (the teachings of which are, as regards the actual definition of these products, entirely included in the present description by way of reference) for the 1,3,5-triazines corresponding to formula (1) and having all of the following characteristics:
$X_1$ is oxygen; $X_2$ is an —NH— radical or oxygen;
$X_3$ is an —NH— radical;
$R_3$ is chosen from: a linear or branched $C_1$–$C_{18}$ alkyl radical; a $C_5$–$C_{12}$ cycloalkyl radical optionally substituted with one or more $C_1$–$C_4$ alkyl radicals;
$R_1$ is chosen from: hydrogen; an alkali metal; an ammonium radical; a radical of formula (4); a linear or branched $C_1$–$C_{18}$ alkyl radical; a $C_5$–$C_{12}$ cycloalkyl radical optionally substituted with one or more $C_1$–$C_4$ alkyl radicals;

if X₂ is an —NH— radical, then R₂ is chosen from: a linear or branched $C_1$–$C_{18}$ alkyl radical; a $C_5$–$C_{12}$ cycloalkyl radical optionally substituted with one or more $C_1$–$C_4$ alkyl radicals;

if X₂ is oxygen, then R₂ is chosen from: hydrogen; a radical of formula (4); a linear or branched $C_1$–$C_{18}$ alkyl radical; a $C_5$–$C_{12}$ cycloalkyl radical optionally substituted with one or more $C_1$–$C_4$ alkyl radicals.

A third preferred family of 1,3,5-triazine derivatives according to the invention is the one described in particular in EP-A-0,796,851 (the teachings of which are, as regards the actual definition of these products, entirely included in the present description by way of reference) for the 1,3,5-triazines corresponding to formula (1) and having all of the following characteristics:

X₁, X₂ and X₃ simultaneously denote —NR—;

the radicals R, which may be identical or different, denote hydrogen or a linear or branched $C_1$–$C_{18}$ alkyl radical or a $C_5$–$C_{12}$ cycloalkyl radical which may be substituted with one or more $C_1$–$C_4$ alkyl radicals;

R₁, R₂ and R₃, which may be identical or different, denote hydrogen or a radical R.

A preferred 1,3,5-triazine is 2,4,6-tris[p-(2'-ethylhexyl-1'-oxycarbonyl)anilino]-1,3,5-triazine which is a screening agent known per se, which is active in the UV-B range, which is in solid form and which is sold in particular under the trademark "UVINUL T150" by BASF. This product corresponds to the following formula:

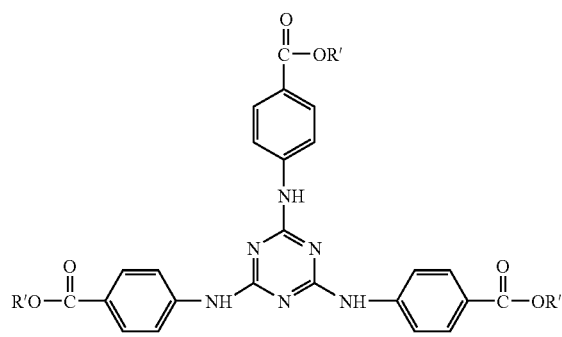

in which R' denotes a 2-ethylhexyl radical.

Another 1,3,5-triazine derivative according to the invention that is particularly preferred is the one corresponding to formula (A) below:

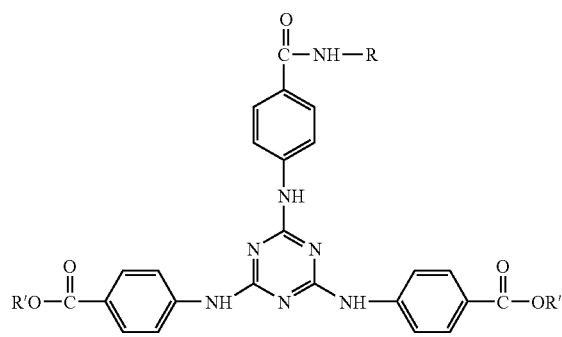

(A)

in which R' denotes a 2-ethylhexyl radical and R denotes a tert-butyl radical.

Among the cinnamic acid derivatives mentioned above, mention may be made especially, in a non-limiting manner, of the following compounds, denoted by their INCI name, and also mixtures thereof:

Ethylhexyl methoxycinnamate sold especially under the trademark PARSOL MCX by Hoffmann LaRoche,
Isopropyl methoxycinnamate,
Isoamyl methoxycinnamate sold under the trademark Neo Heliopan E 1000 by Haarmann & Reimer,
Cinoxate,
DEA methoxycinnamate,
Diisopropyl methylcinnamate,
Glyceryl ethylhexanoate dimethoxycinnamate.

Mention will also be made of silicone cinnamates optionally bearing hydroxyl, $C_1$–$C_6$ alkyl or alkoxy, amino or mono- or di($C_1$–$C_6$)alkylamino substituents.

The amino-substituted hydroxybenzophenones may be chosen from amino 2-hydroxybenzophenones such as those described in EP-1,046,391 and DE-1-00,12,408, and especially n-hexyl 2-(4-diethyl-amino-2-hydroxybenzoyl)benzoate.

The compositions according to the invention advantageously comprise a screening system comprising at least one dibenzoyl-methane derivative and at least one block copolymer chosen from the following block copolymers:
polystyrene/polyoxyethylene
polymethyl methacrylate/polyoxyethylene
polybutyl methacrylate/polyoxyethylene
polyoxybutylene/polyoxyethylene
polycaprolactone/polyoxyethylene
polyethylene/polyoxyethylene
polyoxyethylene/polyoxybutylene/polyoxy-ethylene.

The weight ratio of the nonionic hydrophilic polymer block(s) to the hydrophobic polymer block(s) may be between 1/100 and 50/1.

The dibenzoylmethane derivative(s) may be chosen from those described above.

The screening system present in the compositions according to the invention may also contain one or more compounds chosen from 1,3,5-triazine derivatives, cinnamic acid derivatives and amino-substituted hydroxybenzophenones. These compounds may be chosen from those described above.

The weight concentration ratio between the screening system and the block copolymer(s) used according to the invention is preferably between 0.005 and 0.5.

Preferably, care will be taken to select the amount of block copolymer and of screening system such that the screening system is uniformly dispersed, i.e., without any recrystallization of the dibenzoylmethane derivative being observed after one day at room temperature.

The block copolymer/screening system combination may be prepared by heating the mixture to a temperature required to obtain an isotropic oily mixture. This oily mixture may be used without further modification to form films, or may be cooled. It may then be dispersed in a cosmetic support. Another possible implementation, if the dibenzoylmethane derivative is heat-sensitive, is to dissolve the block copolymer and the dibenzoyl-methane derivative in a common solvent, and then to evaporate the said solvent. The mixture obtained may be treated as previously.

The compositions according to the invention may or may not contain water. In the case of a hydrated composition, the weight concentration ratio between the screening system and the block copolymer(s) is especially between 0.005 and 0.2.

The method for implementing the block copolymer(s) and the screening system to be combined will be chosen by a person skilled in the art as a function of the chemical nature of the polymer. Examples that will be mentioned include nanoprecipitation via a water-miscible solvent, dialysis or direct hydration of the pre-combined block copolymer/screening system mixture. Nanoprecipitation entails co-dissolving, in a water-miscible organic solvent with a boiling point below that of water, the block copolymer(s) and the screening system and in introducing this organic solution more or less quickly into an aqueous phase, with stirring (for example using a magnetic bar, paddles or a turbomixer). The micelles or particles form instantaneously. The solvent is then evaporated off.

The dialysis method entails co-dissolving, in a water-miscible to sparingly water-miscible organic solvent with a boiling point higher than that of water, the block copolymer(s) and the screening system. This solution is introduced into a dialysis bag and dialyzed against water. The dialysis water is regularly renewed, until the solvent has been completely dialysed. The same method may be envisaged with surfactants, for instance octyl glucoside, instead of solvent. It is a concentrated aqueous solution of surfactants that dissolves the copolymer(s) and the screening system to give a clear solution. This solution is then dialysed until the surfactant is completely removed.

Another method, known as the Bangham method, which is commonly used for making liposomes, may be used. This entails dissolving, in an organic solvent, the block copolymer(s) and the screening system, and then evaporating off the solvent so as to obtain a uniform mixture of the block copolymer(s) and of the screening system. A rotary evaporator may be used in the laboratory, an atomizer may be used industrially, or any other method for evaporating a solvent may be used. This mixture may then be hydrated directly, with stirring, using an aqueous solution.

In general, any method known to those skilled in the art for synthesizing liposomes and nanoparticles may be used.

The photostabilized cosmetic compositions according to the invention may of course contain, besides the screening system, one or more additional sunscreens that are different from the preceding sunscreens, which are water-soluble, liposoluble or insoluble in the cosmetic solvents commonly used. These screening agents may be chosen from salicylic derivatives, benzylidenecamphor derivatives, triazine derivatives such as those described in U.S. Pat. No. 4,367,390, EP-0,863,145, EP-0,517,104, EP-0,570,838, EP-0,796,851, EP-0,775,698, EP-0,878,469, EP-0,933,376 and EP-0,893,119, benzophenone derivatives, β,β'-diphenylacrylate derivatives, phenyl-benzimidazole derivatives, anthranilic derivatives, imidazoline derivatives, methylenebis(hydroxyphenyl-benzotriazole) derivatives such as those described in U.S. Pat. Nos. 5,237,071, 5,166,355, GB-2,303,549, DE-197,26,184 and EP-0,893,119, p-aminobenzoic acid derivatives, and screening hydrocarbon-based polymers and screening silicones such as those described especially in WO 93/04665.

Examples of such additional UV-A-active and/or UV-B-active, non-photosensitive organic sunscreens that may be mentioned include the following compounds, denoted by their INCI name, and also mixtures thereof:

Para-Aminobenzoic Acid Derivatives:
PABA,
Ethyl PABA,
Ethyl dihydroxypropyl PABA,
Ethylhexyl dimethyl PABA sold in particular under the trademark ESCALOL® 507 by ISP,
Glyceryl PABA,
PEG-25 PABA sold under the trademark UVINUL® P25 by BASF, Salicylic Derivatives:
Homosalate sold under the trademark EUSOLEX® HMS by Rona/EM Industries,
Ethylhexyl salicylate sold under the trademark NEO HELIOPAN® OS by Haarmann and Reimer,
Dipropylene glycol salicylate sold under the trademark DIPSAL® by Scher,
TEA salicylate sold under the trademark NEO HELIOPAN® TS by Haarmann and Reimer, β,β'-Diphenylacrylate Derivatives:
Octocrylene sold in particular under the trademark UVINUL® N539 by BASF,
Etocrylene sold in particular under the trademark UVINUL® N35 by BASF;

Benzophenone Derivatives:
Benzophenone-1 sold under the trademark UVINUL® 400 by BASF,
Benzophenone-2 sold under the trademark UVINUL® D-50 by BASF,
Benzophenone-3 or Oxybenzone sold under the trademark UVINUL® M-40 by BASF,
Benzophenone-4 sold under the trademark UVINUL® MS-40 by BASF,
Benzophenone-5,
Benzophenone-6 sold under the trademark HELISORB® 11 by Norquay,
Benzophenone-8 sold under the trademark SPECTRA-SORB® UV-24 by American Cyanamid,
Benzophenone-9 sold under the trademark UVINUL® DS-49 by BASF,
Benzophenone-12,
n-hexyl 2-(4-diethylamino-2-hydroxybenzoyl) benzoate Benzylidenecamphor Derivatives:
Benzylidenecamphorsulphonic Acid manufactured under the name MEXORYL® SL by Chimex,
Camphorbenzalkonium Methosulphate sold under the name MEXORYL® SO by Chimex,
Terephthalylidenedicamphorsulphonic acid manufactured under the name MEXORYL® SX by Chimex,
Polyacrylamidomethylbenzylidenecamphor manufactured under the name MEXORYL® SW by Chimex,
3-Benzylidenecamphor manufactured under the name MEXORYL® SD by Chimex,
4-Methylbenzylidenecamphor sold under the name EUSOLEX® 6300 by Merck, Phenylbenzimidazole Derivatives:
Phenylbenzimidazolesulphonic acid sold in particular under the trademark EUSOLEX® 232 by Merck,
Benzimidazilate sold under the trademark NEO HELIOPAN® AP by Haarmann and Reimer, Triazine Derivatives:
Anisotriazine sold under the trademark TINOSORB S by Ciba Geigy,
2,4,6-tris(diisobutyl 4'-aminobenzalmalonate)-s-triazine, Phenylbenzotriazole Derivatives:
Drometrizole trisiloxane sold under the trademark SILATRIZOLE® by Rhodia Chimie, Methylenebis(benzotriazolyl)-tetramethylbutylphenol sold in solid form under the trademark MIXXIM® BB/100 by Fairmount Chemical, or in micronized form as an aqueous dispersion under the trademark TINOSORB® M by Ciba Specialty Chemicals, Anthranilic Derivatives:
Menthyl anthranilate sold under the trademark NEO HELIOPAN® MA by Haarmann and Reimer, Imidazoline Derivatives:
Ethylhexyldimethoxybenzylidenedioxoimidazoline propionate, Benzalmalonate Derivatives:
Polyorganosiloxane containing benzalmalonate functions, sold under the trademark PARSOL® SLX by Hoffmann Laroche, 4,4-Diarylbutadiene Derivatives:
1,1-Dicarboxy(2,2'-dimethylpropyl)-4,4-diphenylbutadiene.

The preferred organic UV-screening agents are chosen from the following compounds:
Ethylhexyl salicylate,
Octocrylene,
Phenylbenzimidazolesulphonic acid,
Terephthalylidenedicamphorsulphonic acid,
Benzophenone-3,
Benzophenone-4,
Benzophenone-5,
4-Methylbenzylidene,
Benzimidazilate,
Anisotriazine,
2,4,6-Tris(diisobutyl 4'-aminobenzalmalonate)-s-triazine,
Ethylhexyltriazone,
Diethylhexylbutamidotriazone,
Methylenebis(benzotriazolyl)tetramethylbutyl-phenol,
Drometrizole trisiloxane, and mixtures thereof.

The compositions according to the invention may also contain agents for artificially tanning and/or browning the skin (self-tanning agents), for instance dihydroxy-acetone (DHA).

The compositions according to the invention may also contain pigments or nanopigments (mean size of the primary particles: generally between 5 nm and 100 nm and preferably between 10 and 50 nm) of coated or uncoated metal oxides, for instance nanopigments of titanium oxide (amorphous or crystallized in rutile and/or anatase form), of iron oxide, of zinc oxide, of zirconium oxide or of cerium oxide, which are all photoprotective agents that are well-known per se, acting by physically blocking out (reflection and/or scattering) UV radiation. Standard coating agents are, moreover, alumina and/or aluminum stearate. Such coated or uncoated metal oxide nanopigments are described in particular in EP-A-0,518,772 and EP-A-0,518,773.

The compositions in accordance with the present invention may also contain standard cosmetic adjuvants chosen especially from fatty substances, organic solvents, ionic or nonionic thickeners, softeners, antioxidants, free-radical scavengers, opacifiers, stabilizers, emollients, silicones, α-hydroxy acids, antifoams, moisturizers, vitamins, fragrances, preservatives, surfactants, fillers, sequestering agents, polymers, propellants, acidifying or basifying agents and dyes, or any other ingredient usually used in cosmetics and/or dermatology, in particular for manufacturing antisun compositions in the form of emulsions.

The fatty substances may consist of an oil or a wax or mixtures thereof. The term "oil" means a compound that is liquid at room temperature. The term "wax" means a compound that is solid or substantially solid at room temperature, and whose melting point is generally above 35° C.

Oils that may be mentioned include mineral oils (petroleum jelly); plant oils (sweet almond oil, macadamia oil, black currant seed oil or jojoba oil); synthetic oils, for instance perhydrosqualene, fatty alcohols, fatty acids or fatty esters (for instance the $C_{12}$–$C_{15}$ alcohol benzoate sold under the name "Finsolv TN" by Finetex, octyl palmitate, isopropyl lanolate, triglycerides, including capric/caprylic acid triglycerides), oxyethylenated or oxypropylenated fatty esters and ethers; silicone oils (cyclomethicone with preferably 4 or 5 silicon atoms and polydimethylsiloxane, or PDMS) or fluoro oils, and polyalkylenes.

Waxy compounds that may be mentioned include paraffin, carnauba wax, beeswax and hydrogenated castor oil.

Among the organic solvents that may be mentioned are lower alcohols and polyols.

The thickeners may be chosen especially from crosslinked polyacrylic acids, modified or unmodified guar gums and celluloses, such as hydroxypropyl guar gum, methylhydroxyethylcellulose or hydroxypropyl-methylcellulose, and silicone gums, for instance a polydimethylsiloxane derivative.

The compositions of the invention may be prepared according to the techniques that are well-known to those skilled in the art, in particular those intended for preparing emulsions of the oil-in-water or water-in-oil type.

These compositions may be in particular in the form of a dispersion, especially an aqueous dispersion, a simple or complex emulsion (O/W, W/O, O/W/O or W/O/W emulsion) such as a cream, a milk or a cream-gel, a powder or a solid tube, and may optionally be packaged as an aerosol and be in the form of a mousse or a spray.

When it is an emulsion, the aqueous phase thereof may comprise a nonionic vesicular dispersion prepared according to known processes (Bangham, Standish and Watkins. J. Mol. Biol. 13, 238 (1965), FR-2,315,991 and FR-2,416,008).

The photostabilized cosmetic compositions according to the invention may be used as compositions for protecting the human epidermis or the hair against ultraviolet rays, as antisun compositions or as makeup products.

When the cosmetic compositions according to the invention are used for protecting the human epidermis against UV rays or as antisun compositions, they may be in the form of a gelled oil, a suspension or dispersion in fatty substances, in the form of a nonionic vesicular dispersion or in the form of an emulsion, preferably of oil-in-water type, such as a cream or a milk, or in the form of an ointment, a gel, a solid tube, a stick, an aerosol mousse or a spray, but may also be in the form of a gel or a lotion. The term "lotion" means an oil-free, clear to opalescent aqueous solution.

When the cosmetic compositions according to the invention are used for protecting the hair, they may be in the form of a shampoo, a lotion, a gel, an emulsion or a nonionic vesicular dispersion. They may constitute, for example, a rinse-out composition, to be applied before or after shampooing, before or after dyeing or bleaching, or before, during or after permanent-waving or relaxing the hair, a styling or treating lotion or gel, a blow-drying or hairsetting lotion or gel, or a composition for permanent-waving, relaxing, dyeing or bleaching the hair.

When the cosmetic compositions according to the invention are used as makeup products for the eyelashes, the eyebrows or the skin, such as an epidermal treatment cream, a foundation, a tube of lipstick, an eyeshadow, a makeup rouge, a mascara or an eyeliner, they may be in solid or pasty, anhydrous or aqueous form, for instance oil-in-water or water-in-oil emulsions, nonionic vesicular dispersions or suspensions.

In order to further illustrate the present invention and the advantages thereof, the following specific examples are given, it being understood that same are intended only as illustrative and in nowise limitative. In said examples to follow, all parts and percentages are given by weight, unless otherwise indicated.

Example 1

The mixture below was formulated:

| | |
|---|---|
| Polystyrene/polyoxyethylene block copolymer sold under the name Tegomer SE-1010 (company Goldschmidt, Polym) | 1.20 g |
| Parsol ® 1789 | 0.22 g |

The Parsol® 1789 was dispersed in the Tegomer SE-1010 with heating at 40° C. for 60 minutes. The mixture was allowed to cool to room temperature. The oily mixture was ready for use.

The oily mixture was evaluated in the form of a thin coat of about 10 microns deposited on a glass plate (microscope slide), in the presence of oxygen.

An irradiation was then performed, using an Ostram-Centra Uvimeter equipped with a xenon lamp, under the following conditions:

Energy of the UV-A lamp: 22 J/cm$^2$
Irradiation time of the simulator=20 minutes These conditions correspond to about one hour of solar UV-A sunshine.

The photodegradation was monitored by absorption spectrophotometry. The following results were obtained:
1) The mixture was able to form a film and the quality of the film was not impaired by the irradiation.
2) 100% of the Parsol® 1789 was recovered after this exposure.

The absorption spectrum was not modified after irradiation.

Example 2

The mixture below was formulated:

A block copolymer was dissolved in dichloromethane with excess Parsol® 1789. The solvent was evaporated off under reduced pressure using a rotary evaporator. The film formed was then hydrated with distilled water, with stirring, at a temperature between 20 and 80° C., for two hours. The amount of polymer in the water was about one percent.

24 hours later, this suspension was centrifuged in order to separate out the Parsol® 1789 that had not been encapsulated in the polymer micelles. The supernatant, which should not contain identifiable crystals under an optical microscope in polarized light, was taken up and then assayed by HPLC.

The supernatant was then irradiated under UV for one hour, the UV-A intensity being 3.2 mW/cm$^2$ and the UV-B intensity being 0.22 mW/cm$^2$, i.e., 11.5 J/cm$^2$ and 0.79 J/cm$^2$, respectively, in a 96-well plate, at a rate of 100 μl of suspension per well. A quartz plate was placed on top in order to limit the evaporation. The suspensions were then assayed again by HPLC.

The following results were obtained:

| Block Copolymers (Names and Marketing Companies) | Chemical Nature | Ratio A/B or A/B/A | Residual Percentage of Parsol ® 1789 |
|---|---|---|---|
| SE 10-10 (Goldschmidt) | PS/POE | 1000/1000 | 81% |
| ME 10-10 (Goldschmidt) | Methyl methacrylate/ POE | 1000/1000 | 91.5% |
| BE1010 (Goldschmidt) | Butyl methacrylate/ POE | 1000/1000 | 85% |
| Plonon B208 (NOF) | POE/POB/ POE | 3500/2000/ 3500 | 89% |
| P1044-SOE/P550-SOE (80/20) (Polymer Source) | PS/POE | 3900/5100 12200/23900 | 91.5% |
| P1503-SOE (Polymer Source) | PS/POE | 2300/3100 | 93.8% |
| P2351-EOCL (Polymer Source) | Polycaprolactone/ POE | 800/ 5000 | 83% |
| P972-2EOCL (Polymer Source) | Polycaprolactone/ POE | 1370/ 5000 | 85% |
| P1153-ETEO (Polymer Source) | Polyethylene/ POE | 5000/5900 | 60% |

POE: polyoxyethylene
POB: polyoxybutylene
PS: polystyrene

POE: polyoxyethyene
POB: polyoxyethyene
PS: polystyrene

A mild photodegradation of the Parsol® 1789 with the block copolymers used according to the invention was observed.

Example 3

Compositions tested:

| | Composition A | Composition B | Composition C |
|---|---|---|---|
| Tegomer SE 1010 | 3 | | |
| Tegomer SE3030 | | 3 | |
| Parsol 1789 | 1 | 1 | 1 |
| C$_{12}$/C$_{15}$ alkylbenzoate | 11 | 11 | 11 |
| Crosslinked acrylic acid/(C$_{10}$/C$_{30}$)alkyl acrylate copolymer | 0.15 | 0.15 | 0.15 |
| Hydroxypropylmethyl-cellulose | 0.05 | 0.05 | 0.05 |
| Triethanolamine | 0.15 | 0.15 | 0.15 |
| Water qs | 50 | 50 | 50 |

Tests Performed:

The residual optical density (OD) after spreading, at 0.75 mg/cm$^2$, the compositions onto frosted quartz slides and exposure to UV (Heraeus Sun Test) for a period equivalent to an energy of 18 J/cm$^2$ measured in UVA, was measured.

The plates were then extracted with ethanol and a spectrophotometric assay was performed at a wavelength of 358 nm.

Results:

|  | Composition A | Composition B | Composition C |
|---|---|---|---|
| Residual % of OD at 358 nm | 20 ± 73 | 19.6 ± 1 | 5.4 ± 2 |

A mild photodegradation of the Parsol® 1789 with the block copolymers used according to the invention was observed.

Example 4

| Oil-in-water emulsion: | |
|---|---|
| Oily phase | |
| Diglyceryl monostearate | 2.0% |
| PEG-20 stearate | 1.5% |
| Disodium N-stearoyl-L-glutamic acid | 0.5% |
| (Acyl glutamate HS 21 (Ajinomoto)) | |
| Liquid petroleum jelly | 3% |
| Petroleum jelly | 1% |
| Stearyl heptanoate | 3% |
| Apricot kernel oil | 5% |
| Hydrogenated polyisobutene | 5% |
| Isocetyl palmitate | 2% |
| Volatile silicone | 5% |
| Vitamin E | 0.5% |
| Preservatives | 0.3% |
| Aqueous phase 1: | |
| Glycerol | 5% |
| Preservatives | 1% |
| Distilled water qs | 100% |
| Aqueous phase 2: | |
| Carbomer | 0.4% |
| Distilled water | 15% |
| Preservatives | 0.1% |
| Triethanolamine | 0.4% |
| Aqueous phase 3: | |
| Aqueous suspension of ME 10-10 at 20% in water, containing 8% Parsol 1789 | 10% |

Procedure: Aqueous phase 1 was introduced at 60° C. into the oily phase at 60° C., with very vigorous stirring. The temperature and stirring were maintained for 30 minutes. The suspension was then cooled to room temperature.

Aqueous phase 2 was then dispersed using a non-shear disperser. Aqueous phase 3 (suspension of micelles) was then introduced with gentle stirring.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable photostable sunscreen/photoprotective composition, comprising at least one dibenzoylmethane UV-sunscreen and an effective photostabilizing amount therefor of at least one amphiphilic block copolymer which comprises at least one nonionic hydrophilic polymer block and at least one hydrophobic polymer block, formulated into a topically applicable, cosmetically acceptable medium therefor.

2. The photostable sunscreen/photoprotective composition as defined by claim 1, wherein the weight ratio of said at least one nonionic hydrophilic polymer block to said at least one hydrophobic polymer block ranges from 1/100 to 50/1.

3. The photostable sunscreen/photoprotective composition as defined by claim 1, wherein the weight concentration ratio between the UV-screening agents therein and said at least one amphiphilic block copolymer ranges from 0.005 to 0.5.

4. The photostable sunscreen/photoprotective composition as defined by claim 1, said at least one nonionic hydrophilic polymer block comprising polyethylene oxide or polyvinylpyrrolidone.

5. The photostable sunscreen/photoprotective composition as defined by claim 1, said at least one hydrophobic polymer block comprising polystyrene, poly(tert-butylstyrene), poly(methyl methacrylate), poly(ethyl acrylate), poly(butyl acrylate), poly(butyl methacrylate), poly(vinyl acetate), polycaprolactones, polycaprolactams, polydimethylsiloxanes, poly($C_3$–$C_6$ alkylene oxides), poly(aspartic acid), poly(lactic acid), poly(glycolic acid), polyleucine, polybutadiene, polyethylene, polypropylene or polybutylene.

6. The photostable sunscreen/photoprotective composition as defined by claim 1, said at least one amphiphilic block copolymer comprising:
polystyrene/polyoxyethylene,
polymethyl methacrylate/polyoxyethylene,
polybutyl methacrylate/polyoxyethylene,
polyoxybutylene/polyoxyethylene,
polycaprolactone/polyoxyethylene,
polyethylene/polyoxyethylene, or
polyoxyethylene/polyoxybutylene/polyoxyethylene.

7. The photostable sunscreenlphotoprotective composition as defined by claim 1, said at least one dibenzoylmethane UV-sunscreen comprising:
2-methyldibenzoylmethane,
4-methyldibenzoylmethane,
4-isopropyldibenzoylmethane,
4-tertbutyldibenzoylmethane,
2,4-dimethyldibenzoylmethane,
2,5-dimethyldibenzoylmethane,
4,4-diisopropyldibenzoylmethane,
4,4-dimethoxydibenzoylmethane,
4-tert-butyl-4'-methoxydibenzoylmethane,
2-methyl-5-isopropyl-4'-methoxydibenzoylmethane,
2-methyl-5-tert-butyl-4'-methoxydibenzoylmethane,
2,4-dimethyl-4'-methoxydibenzoylmethane, or
2,6-dimethyl-4-tert-butyl-4'-methoxydibenzoylmethane.

8. The photostable sunscreen/photoprotective composition as defined by claim 1, said at least one dibenzoylmethane UV-sunscreen comprising 4-tert-butyl-4'-methoxydibenzoylmethane.

9. The photostable sunscreen/photoprotective composition as defined by claim 1, further comprising at least one 1,3,5-triazine UV-sunscreen, cinnamic acid UV-sunscreen and/or amino-substituted hydroxybenzophenone UV-sunscreen.

10. The photostable sunscreen/photoprotective composition as defined by claim 1, further comprising at least one UV-sunscreen selected from the group consisting of salicylic derivatives, dibenzylidenecamphor derivatives, benzophenone derivatives, β,β'-diphenylacrylate derivatives, phenylbenzimidazole derivatives, anthranilic derivatives, imidazoline derivatives, methylenebis(hydroxyphenylbenzotriazole) derivatives, p-aminobenzoic acid derivatives, screening hydrocarbon-based polymers and screening silicones.

11. The photostable sunscreenlphotoprotective composition as defined by claim 1, further comprising at least one optionally coated metal oxide nanopigment.

12. The photostable sunscreenlphotoprotective composition as defined by claim 11, said at least one optionally coated metal oxide nanopigment comprising titanium oxide, iron oxide, zinc oxide, zirconium oxide and/or cerium oxide.

13. The photostable sunscreen/photoprotective composition as defined by claim 1, further comprising at least one agent for artificially tanning and/or browning the skin.

14. The photostable sunscreen/photoprotective composition as defined by claim 1, further comprising at least one additive or adjuvant selected from the group consisting of fatty substances, organic solvents, thickeners, antioxidants, opacifiers, stabilizers, antifoams, fragrances, preservatives, fillers, sequestering agents, propellants and dyes.

15. The photostable sunscreen/photoprotective composition as defined by claim 1, in anhydrous state.

16. The photostable sunscreen/photoprotective composition as defined by claim 1, in hydrated state.

17. The photostable sunscreen/photoprotective composition as defined by claim 3, wherein the weight concentration ratio between the UV-screening agents therein and said at least one amphiphilic block copolymer ranges from 0.005 to 0.2.

18. The photostable sunscreen/photoprotective composition as defined by claim 1, formulated as a gelled oil, a suspension or dispersion in a fatty substance, a nonionic vesicular dispersion, an emulsion, a cream, a milk, an ointment, a gel, a solid tube or stick, a mousse, a spray, or a lotion.

19. The photostable sunscreen/photoprotective composition as defined by claim 1, formulated as a makeup for the eyelashes, the eyebrows, or the skin.

20. The photostable sunscreen/photoprotective composition as defined by claim 1, formulated as a rinse-out composition, to be applied before or after shampooing, before or after dyeing or bleaching, or before, during or after permanent-waving or relaxing the hair, a styling or treating lotion or gel, a blow-drying or hairsetting lotion or gel, or a composition for permanent-waving, relaxing, dyeing or bleaching the hair.

21. A process for UV-photostablizing a sunscreen/photoprotective composition which comprises at least one dibenzoylmethane UV-sunscreen, comprising formulating therewith a thus effective amount of at least one amphiphilic block copolymer which comprises at least one nonionic hydrophilic polymer block and at least one hydrophobic polymer block.

22. The process as defined by claim 21, wherein the weight ratio of said at least one nonionic hydrophilic polymer block to said at least one hydrophobic polymer block ranges from 1/100 to 50/1.

23. The process as defined by claim 21, wherein the weight concentration ratio between the UV-screening agents therein and said at least one amphiphilic block copolymer ranges from 0.005 to 0.5.

24. The process as defined by claim 21, said at least one nonionic hydrophilic polymer block comprising polyethylene oxide or polyvinylpyrrolidone.

25. The process as defined by claim 21, said at least one hydrophobic polymer block comprising polystyrene, poly (tert-butylstyrene), poly(methyl methacrylate), poly(ethyl acrylate), poly(butyl acrylate), poly(butyl methacrylate), poly(vinyl acetate), polycaprolactones, polycaprolactams, polydimethylsiloxanes, poly($C_3$–$C_6$ alkylene oxides), poly (aspartic acid), poly(lactic acid), poly(glycolic acid), polyleucine, polybutadiene, polyethylene, polypropylene or polybutylene.

26. The process as defined by claim 21, said at least one amphiphilic block copolymer comprising:
polystyrene/polyoxyethylene,
polymethyl methacrylate/polyoxyethylene,
polybutyl methacrylate/polyoxyethylene,
polyoxybutylene/polyoxyethylene,
polycaprolactone/polyoxyethylene,
polyethylene/polyoxyethylene, or
polyoxyethylene/polyoxybutylene/polyoxyethylene.

27. The process as defined by claim 21, said at least one dibenzoylmethane UV-sunscreen comprising:
2-methyldibenzoylmethane,
4-methyldibenzoylmethane,
4-isopropyldibenzoylmethane,
4-tertbutyldibenzoylmethane,
2,4-dimethyldibenzoylmethane,
2,5-dimethyldibenzoylmethane,
4,4-diisopropyldibenzoylmethane,
4,4-dimethoxydibenzoylmethane,
4-tert-butyl-4'-methoxydibenzoylmethane,
2-methyl-5-isopropyl-4'-methoxydibenzoylmethane,
2-methyl-5-tert-butyl-4'-methoxydibenzoylmethane,
2,4-dimethyl-4'-methoxydibenzoylmethane, or
2,6-dimethyl-4-tert-butyl-4'-methoxydibenzoylmethane.

28. The process as defined by claim 21, said at least one dibenzoylmethane UV-sunscreen comprising 4-tert-butyl-4'-methoxydibenzoylmethane.

29. A regime or regimen for photoprotecting human skin against the damaging effects of UV-radiation, comprising topically applying thereon a thus effective amount of the photostable sunscreen/photoprotective composition as defined by claim 1.

30. A regime or regimen for photoprotecting human skin against the damaging effects of UV-radiation, comprising topically applying thereon a thus effective amount of the photostable sunscreenlphotoprotective composition as defined by claim 4.

31. A regime or regimen for photoprotecting human skin against the damaging effects of UV-radiation, comprising topically applying thereon a thus effective amount of the photostable sunscreen/photoprotective composition as defined by claim 5.

32. A regime or regimen for photoprotecting human skin against the damaging effects of UV-radiation, comprising topically applying thereon a thus effective amount of the photostable sunscreen/photoprotective composition as defined by claim 6.

33. A regime or regimen for photoprotecting human skin against the damaging effects of UV-radiation, comprising topically applying thereon a thus effective amount of the photostable sunscreen/photoprotective composition as defined by claim 7.

34. A regime or regimen for photoprotecting human skin against the damaging effects of UV-radiation, comprising topically applying thereon a thus effective amount of the photostable sunscreen/photoprotective composition as defined by claim 8.

* * * * *